US00RE33989E

United States Patent [19]

Wenderoth et al.

[11] E Patent Number: Re. 33,989

[45] Reissued Date of Patent: Jul. 7, 1992

[54] OXIME ETHERS AND FUNGICIDES CONTAINING THESE COMPOUNDS

[75] Inventors: Bernd Wenderoth, Lampertheim; Timm Anke, Kaiserslautern; Costi Rentzes, Heidelberg; Eberhard Ammermann, Ludwigshafen; Ernst-Heinrich Pommer, Limburgerhof; Wolfgang Steglich, Bonn-Roettgen, all of Fed. Rep. of Germany

[73] Assignee: BASF Aktiengesellschaft, Ludwigshafen, Fed. Rep. of Germany

[21] Appl. No.: 540,817

[22] Filed: Jun. 11, 1990

Related U.S. Patent Documents

Reissue of:

[64] Patent No.: 4,829,085
Issued: May 9, 1989
Appl. No.: 198,715
Filed: May 25, 1988

U.S. Applications:

[63] Continuation of Ser. No. 69,224, Jul. 2, 1987, abandoned.

[30] Foreign Application Priority Data

Jul. 16, 1986 [DE] Fed. Rep. of Germany ..... 3623921

[51] Int. Cl.[5] ..... A61K 31/275

[52] U.S. Cl. ..... 514/522; 514/539; 514/567; 558/412; 558/414; 562/435; 562/440; 560/21; 560/35

[58] Field of Search ..... 515/552, 539, 567; 558/412, 414; 560/21, 35; 562/435, 440

[56] References Cited

U.S. PATENT DOCUMENTS

| | | | |
|---|---|---|---|
| 3,932,385 | 1/1976 | Cook et al. | 514/539 |
| 4,415,743 | 11/1983 | Martin | 547/491 |
| 4,482,496 | 11/1984 | Weber | 560/35 |
| 4,490,167 | 12/1984 | Pissiotas et al. | 71/105 |
| 4,598,756 | 10/1985 | Martin | 560/35 |
| 4,708,734 | 11/1987 | Hoyashi et al. | 560/35 |

FOREIGN PATENT DOCUMENTS

| | | | |
|---|---|---|---|
| 1404221 | 8/1975 | United Kingdom | 562/440 |

*Primary Examiner*—James H. Reamer
*Attorney, Agent, or Firm*—Oblon, Spivak, McClelland, Maier & Neustadt

[57] ABSTRACT

Oxime ethers of the formula (I)

where $R^1$ and $R^2$ are hydrogen or alkyl, X(m=1 to 5) is halogen, cyano, trifluoromethyl, nitro, allyl, alkoxy, unsubstituted or substituted phenyl, unsubstituted or substituted phenoxy, unsubstituted or substituted benzyloxy or hydrogen, and Y is methyleneoxy, oxymethylene, ethylene, ethynylene or oxygen, and fungicides containing these compounds.

32 Claims, No Drawings

OXIME ETHERS AND FUNGICIDES CONTAINING THESE COMPOUNDS

Matter enclosed in heavy brackets [ ] appears in the original patent but forms no part of this reissue specification; matter printed in italics indicates the additions made by reissue.

This application is a continuation of application Ser. No. 069,224, filed on July 2, 1987, now abandoned.

The present invention relates to novel oxime ether derivatives, their preparation and their use as fungicides.

It is known that N-tridecyl-2,6-dimethylmorpholine and its salts, for example the acetate, can be used as fungicides (DE-1 164 152 and 1 173 722). However, their action is inadequate in some cases. It is also known that acrylic acid derivatives, e.g. methyl 2-(4-[p-chlorostyryl]-phenyl)-3-methoxyacrylate, can be used as fungicides (European Pat. No. 178,826). However, their action is unsatisfactory.

We have found that novel oxime ether derivatives of the formula I

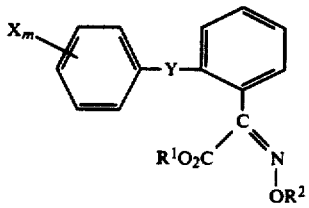

(I)

where $R^1$ and $R^2$ are identical or different and are each hydrogen or alkyl of 1 to 5 carbon atoms, the radicals X (m = 1 to 5) are identical or different substituents from the group consisting of halogen, cyano, trifluoromethyl, nitro, $C_1$–$C_4$-alkyl, $C_1$–$C_4$-alkoxy, unsubstituted or substituted phenyl, unsubstituted or substituted phenoxy, unsubstituted or substituted benzyloxy and hydrogen, and Y is methyleneoxy, oxymethylene, ethylene, ethenylene, ethynylene or oxygen, not only possess very high fungitoxic activity but also are very well tolerated by plants.

Because of the C=N double bond, the novel compounds of the formula I are obtained in their preparation in the form of E/Z isomer mixtures, which can be separated into the individual components in a conventional manner, for example by crystallization or chromatography. The invention relates both to the individual isomeric compounds and to mixtures of these.

$R^1$ is preferably hydrogen or $C_1$–$C_3$-alkyl, such as methyl, ethyl or isopropyl, and $R^2$ is preferably hydrogen or $C_1$–$C_5$-alkyl, such as methyl, ethyl, n-propyl, isopropyl, n-butyl, sec-butyl, isobutyl, tert-butyl, n-pentyl or neopentyl.

X is preferably hydrogen, 2-fluoro, 3-fluoro, 4-fluoro, 2-chloro-6-fluoro, 2-chloro, 3-chloro, 4-chloro, 2-bromo, 3-bromo, 4-bromo, 2,4-dichloro, 2,6-dichloro, 3,5-dichloro, 2,4,6-trichloro, 2-chloro-4-methyl, 2-methyl-4-chloro, 2-methyl, 3-methyl, 4-methyl, 4-ethyl, 4-isopropyl, 4-tert-butyl, 2,4-dimethyl, 2,6-dimethyl, 2,4,6-trimethyl, 2-methoxy-4-methyl, 4-methoxy-2-methyl, 2-methoxy, 3-methoxy, 4-methoxy, 4-ethoxy, 4-isopropoxy, 2-trifluoromethyl, 3-trifluoromethyl, 4-trifluoromethyl, 2-cyano, 4-cyano, 3-nitro, 4-nitro, 4-phenyl, 4-benzyloxy, 4-phenoxy, halophenoxy, 4(2-chlorophenoxy), 4-(2,4-dichlorophenoxy), $C_1$–$C_4$-alkylphenoxy, 4-(2-methylphenoxy), 3-benzyloxy, halobenzyloxy, 3-(2-chlorobenzyloxy), 3-(2,4-dichlorobenzyloxy), 3-(2-fluorobenzyloxy), 3-(4-bromobenzyloxy), $C_1$–$C_4$-alkylbenzyloxy, 3-(2-methylbenzyloxy), 3-phenoxy, 3-(2-chlorophenoxy), 3-(2,4-dichlorophenoxy), 3-(2-fluorophenoxy), 3-(4-bromophenoxy) or 3-(2-methylphenoxy), and Y is preferably a —$CH_2O$—, —$OCH_2$—, —$CH_2$—$CH_2$—, —CH=CH— or —C≡C— group or O.

The novel compounds can be prepared by reacting an α-ketocarboxylate of the formula II

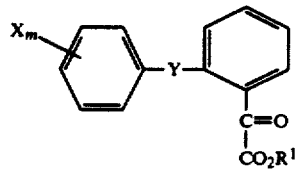

(II)

where $X_m$, Y and $R^1$ have the above meanings, (a) with an O-substituted hydroxylamine of the general formula III $$H_2N—O—R^2 \quad \text{(III)}$$

where $R^2$ has the above meanings, or (b) with hydroxylamine to give the corresponding oxime, and then reacting the product with a halogen derivative of the formula IV $$R^2—X \quad \text{(IV)}$$

wherein $R^2$ has the above meanings and X is halogen (F, Cl, Br or I), or with a dialkyl sulfate.

The α-ketocarboxylates of the formula II can be prepared, for example, by reacting the corresponding aromatic Grignard compounds with imidazolides of the formula V

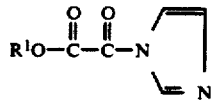

(V)

where $R^1$ has the above meanings (J. S. Nimitz and H. S. Mosher, J. Org. Chem. 46 (1981), 211–213.

The Example which follows illustrates the preparation of the novel compounds of the formula I.

(a) Preparation of methyl 2-(benzyloxy)-phenylglyoxylate 0.1 mole of a Grignard compound prepared from 1-benzyloxy-2-bromobenzene and magnesium turnings in tetrahydrofuran is slowly added dropwise 14.6 g (95 millimoles) of methyloxalylimidazole in tetrahydrofuran under nitrogen at −50° C. The mixture is allowed to come slowly to room temperature (20° C.) over a period of 4 hours. It is poured onto ice water and extracted several times each ether. The combined ether phases are washed neutral and dried. After the solvent has been evaporated off, the product is brought to crystallization with n-pentane to give 16 g (62%) of colorless crystals of the abovementioned compound.

$^1$H-NMR($CDCL_3$): δ = 3.35 (s,3H), 5.07 (s,2H), 7.05 (m,2H), 7.40(m,5H), 7.55 (m,1H), 7.90 (m,1H).

(b) Preparation of (Z)-(2-benzyloxyphenyl)-glyoxylic acid methyl ester O-methyloxime (compound no. 83)

15.5 g (57 millimoles) of methyl 2-(benzyloxy)phenylglyoxylate in 160 ml of methanol are initially taken, and 11.5 g of sodium carbonate and 9.45 g (114 millimoles) of O-methylhydroxylamine hydrochloride are added. The stirred mixture is refluxed for 24 hours. 100 ml of water are added, after which the mixture is extracted several times with ethyl acetate and the ethyl acetate solution is dried with $Na_2SO_4$ and then evaporated down.

11 g (65%) of the abovementioned compound are obtained in the form of an isomer mixture. Mixing with n-pentane gives the pure (Z)-isomer as white crystals of melting point 120°-132° C.

$^{13}$C-NMR ($CDCL_3$):$\delta$=52.50, 62.92, 70.93, 112.60, 120.49, 121.33, 128.19, 128.52 (2c) 129.04 (3C), 131.70, 135.92, 148.44, 156.50, 163.84.

The compounds listed in the Table below can be prepared by appropriately modifying the above data.

(I)

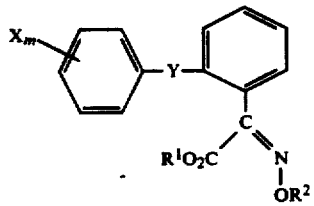

| Comp. No. | $X_m$ | Y | $R^1$ | $R^2$ | Isomer | Mp(°C.) | IR($cm^{-1}$) |
|---|---|---|---|---|---|---|---|
| 1 | H | $-CH_2-CH_2-$ | $CH_3$ | $CH_3$ | | | |
| 2 | 2-F | $-CH_2-CH_2-$ | $CH_3$ | $CH_3$ | | | |
| 3 | 3-F | $-CH_2-CH_2-$ | $CH_3$ | $CH_3$ | | | |
| 4 | 4-F | $-CH_2-CH_2-$ | $CH_3$ | $CH_3$ | | | |
| 5 | 2-Cl, 6-F | $-CH_2-CH_2-$ | $CH_3$ | $CH_3$ | | | |
| 6 | 2-Cl | $-CH_2-CH_2-$ | $CH_3$ | $CH_3$ | | | |
| 7 | 3-Cl | $-CH_2-CH_2-$ | $CH_3$ | $CH_3$ | | | |
| 8 | 4-Cl | $-CH_2-CH_2-$ | $CH_3$ | $CH_3$ | | | |
| 9 | 2-Br | $-CH_2-CH_2-$ | $CH_3$ | $CH_3$ | | | |
| 10 | 3-Br | $-CH_2-CH_2-$ | $CH_3$ | $CH_3$ | | | |
| 11 | 4-Br | $-CH_2-CH_2-$ | $CH_3$ | $CH_3$ | | | |
| 12 | 2,4-$Cl_2$ | $-CH_2-CH_2-$ | $CH_3$ | $CH_3$ | | | |
| 13 | 2,6-$Cl_2$ | $-CH_2-CH_2-$ | $CH_3$ | $CH_3$ | | | |
| 14 | 3,5-$Cl_2$ | $-CH_2-CH_2-$ | $CH_3$ | $CH_3$ | | | |
| 15 | 2,4,6-$Cl_3$ | $-CH_2-CH_2-$ | $CH_3$ | $CH_3$ | | | |
| 16 | 2-Cl, 4-$CH_3$ | $-CH_2-CH_2-$ | $CH_3$ | $CH_3$ | | | |
| 17 | 2-$CH_3$, 4-Cl | $-CH_2-CH_2-$ | $CH_3$ | $CH_3$ | | | |
| 18 | 2-$CH_3$ | $-CH_2-CH_2-$ | $CH_3$ | $CH_3$ | | | |
| 19 | 3-$CH_3$ | $-CH_2-CH_2-$ | $CH_3$ | $CH_3$ | | | |
| 20 | 4-$CH_3$ | $-CH_2-CH_2-$ | $CH_3$ | $CH_3$ | | | |
| 21 | 4-$C_2H_5$ | $-CH_2-CH_2-$ | $CH_3$ | $CH_3$ | | | |
| 22 | 4-i-$C_3H_7$ | $-CH_2-CH_2-$ | $CH_3$ | $CH_3$ | | | |
| 23 | 4-t-$C_4H_9$ | $-CH_2-CH_2-$ | $CH_3$ | $CH_3$ | | | |
| 24 | 2,4-$(CH_3)_2$ | $-CH_2-CH_2-$ | $CH_3$ | $CH_3$ | | | |
| 25 | 2,6-$(CH_3)_2$ | $-CH_2-CH_2-$ | $CH_3$ | $CH_3$ | | | |
| 26 | 2,4,6-$(CH_3)_3$ | $-CH_2-CH_2-$ | $CH_3$ | $CH_3$ | | | |
| 27 | 2-$OCH_3$, 4-$CH_3$ | $-CH_2-CH_2-$ | $CH_3$ | $CH_3$ | | | |
| 28 | 4-$OCH_3$, 2-$CH_3$ | $-CH_2-CH_2-$ | $CH_3$ | $CH_3$ | | | |
| 29 | 2-$OCH_3$ | $-CH_2-CH_2-$ | $CH_3$ | $CH_3$ | | | |
| 30 | 3-$OCH_3$ | $-CH_2-CH_2-$ | $CH_3$ | $CH_3$ | | | |
| 31 | 4-$OCH_3$ | $-CH_2-CH_2-$ | $CH_3$ | $CH_3$ | | | |
| 32 | 4-$OC_2H_5$ | $-CH_2-CH_2-$ | $CH_3$ | $CH_3$ | | | |
| 33 | 4-O-i-$C_3H_7$ | $-CH_2-CH_2-$ | $CH_3$ | $CH_3$ | | | |
| 34 | 2-$CF_3$ | $-CH_2-CH_2-$ | $CH_3$ | $CH_3$ | | | |
| 35 | 3-$CF_3$ | $-CH_2-CH_2-$ | $CH_3$ | $CH_3$ | | | |
| 36 | 4-$CF_3$ | $-CH_2-CH_2-$ | $CH_3$ | $CH_3$ | | | |
| 37 | 2-CN | $-CH_2-CH_2-$ | $CH_3$ | $CH_3$ | | | |
| 38 | 4-CN | $-CH_2-CH_2-$ | $CH_3$ | $CH_3$ | | | |
| 39 | 3-$NO_2$ | $-CH_2-CH_2-$ | $CH_3$ | $CH_3$ | | | |
| 40 | 4-$NO_2$ | $-CH_2-CH_2-$ | $CH_3$ | $CH_3$ | | | |
| 41 | 4-$C_6H_5$ | $-CH_2-CH_2-$ | $CH_3$ | $CH_3$ | | | |
| 42 | H | $-CH=CH-$ | $CH_3$ | $CH_3$ | Z | oil | 2960, 1740, 1496, 1455, 1227, 1043, 1017, 962, 760, 692 |
| 43 | 2-F | $-CH=CH-$ | $CH_3$ | $CH_3$ | | | |
| 44 | 3-F | $-CH=CH-$ | $CH_3$ | $CH_3$ | | | |
| 45 | 4-F | $-CH=CH-$ | $CH_3$ | $CH_3$ | | | |
| 46 | 2-Cl, 6-F | $-CH=CH-$ | $CH_3$ | $CH_3$ | | | |
| 47 | 2-Cl | $-CH=CH-$ | $CH_3$ | $CH_3$ | | | |
| 48 | 3-Cl | $-CH=CH-$ | $CH_3$ | $CH_3$ | | | |
| 49 | 4-Cl | $-CH=CH-$ | $CH_3$ | $CH_3$ | E/Z | oil | 2970, 1740, 1492, 1456, 1228, 1091, |

-continued (I)

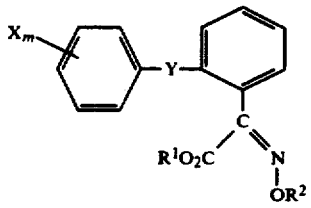

| Comp. No. | $X_m$ | Y | $R^1$ | $R^2$ | Isomer | Mp(°C.) | IR($cm^{-1}$) |
|---|---|---|---|---|---|---|---|
| | | | | | | | 1044, 1013, 962, 813 753 |
| 50 | 2-Br | —CH=CH— | $CH_3$ | $CH_3$ | | | |
| 51 | 3-Br | —CH=CH— | $CH_3$ | $CH_3$ | | | |
| 52 | 4-Br | —CH=CH— | $CH_3$ | $CH_3$ | | | |
| 53 | 2,4-$Cl_2$ | —CH=CH— | $CH_3$ | $CH_3$ | | | |
| 54 | 2,6-$Cl_2$ | —CH=CH— | $CH_3$ | $CH_3$ | | | |
| 55 | 3,5-$Cl_2$ | —CH=CH— | $CH_3$ | $CH_3$ | | | |
| 56 | 2,4,6-$Cl_3$ | —CH=CH— | $CH_3$ | $CH_3$ | | | |
| 57 | 2-Cl, 4-$CH_3$ | —CH=CH— | $CH_3$ | $CH_3$ | | | |
| 58 | 2-$CH_3$, 4-Cl | —CH=CH— | $CH_3$ | $CH_3$ | | | |
| 59 | 2-$CH_3$ | —CH=CH— | $CH_3$ | $CH_3$ | | | |
| 60 | 3-$CH_3$ | —CH=CH— | $CH_3$ | $CH_3$ | | | |
| 61 | 4-$CH_3$ | —CH=CH— | $CH_3$ | $CH_3$ | | | |
| 62 | 3-$CH_3$ | —CH=CH— | $CH_3$ | $CH_3$ | | | |
| 63 | 4-i-$C_3H_7$ | —CH=CH— | $CH_3$ | $CH_3$ | | | |
| 64 | 4-t-$C_4H_9$ | —CH=CH— | $CH_3$ | $CH_3$ | | | |
| 65 | 2,4-$(CH_3)_2$ | —CH=CH— | $CH_3$ | $CH_3$ | | | |
| 66 | 2,6-$(CH_3)_2$ | —CH=CH— | $CH_3$ | $CH_3$ | | | |
| 67 | 2,4,6-$(CH_3)_3$ | —CH=CH— | $CH_3$ | $CH_3$ | | | |
| 68 | 2-$OCH_3$, 4-$CH_3$ | —CH=CH— | $CH_3$ | $CH_3$ | | | |
| 69 | 4-$OCH_3$, 2-$CH_3$ | —CH=CH— | $CH_3$ | $CH_3$ | | | |
| 70 | 2-$OCH_3$ | —CH=CH— | $CH_3$ | $CH_3$ | | | |
| 71 | 3-$OCH_3$ | —CH=CH— | $CH_3$ | $CH_3$ | | | |
| 72 | 4-$OCH_3$ | —CH=CH— | $CH_3$ | $CH_3$ | | | |
| 73 | 4-$OC_2H_5$ | —CH=CH— | $CH_3$ | $CH_3$ | | | |
| 74 | 4-O-i$C_3H_7$ | —CH=CH— | $CH_3$ | $CH_3$ | | | |
| 75 | 2-$CF_3$ | —CH=CH— | $CH_3$ | $CH_3$ | | | |
| 76 | 3-$CF_3$ | —CH=CH— | $CH_3$ | $CH_3$ | | | |
| 77 | 4-$CF_3$ | —CH=CH— | $CH_3$ | $CH_3$ | | | |
| 78 | 2-CN | —CH=CH— | $CH_3$ | $CH_3$ | | | |
| 79 | 4-CN | —CH=CH— | $CH_3$ | $CH_3$ | | | |
| 80 | 3-$NO_2$ | —CH=CH— | $CH_3$ | $CH_3$ | | | |
| 81 | 4-$NO_2$ | —CH=CH— | $CH_3$ | $CH_3$ | | | |
| 82 | 4-$C_6H_5$ | —CH=CH— | $CH_3$ | $CH_3$ | | | |
| 83 | H | —$CH_2O$— | $CH_3$ | $CH_3$ | Z | 129–132 | 2940, 1737 1489, 1455 1343, 1278 1234, 1045 1027, 758 |
| 84 | 2-F | —$CH_2O$— | $CH_3$ | $CH_3$ | | | |
| 85 | 3-F | —$CH_2O$— | $CH_3$ | $CH_3$ | E/Z | 46–48 | 2970, 1734, 1592, 1492, 1452, 1278, 1231, 1028, 755 |
| 86 | 4-F | —$CH_2O$— | $CH_3$ | $CH_3$ | E/Z | 97–99 | 2970, 1740, 1600, 1513, 1487, 1276, 1224, 1042, 1025, 879, 751 |
| 87 | 2-Cl, 6-F | —$CH_2O$— | $CH_3$ | $CH_3$ | | | |
| 88 | 2-Cl | —$CH_2O$— | $CH_3$ | $CH_3$ | | | |
| 89 | 3-Cl | —$CH_2O$— | $CH_3$ | $CH_3$ | E/Z | oil | 2970, 1742, 1600, 1490, 1453, 1279, 1228, 1044, 1024, 759 |
| 90 | 4-Cl | —$CH_2O$— | $CH_3$ | $CH_3$ | Z | 106–109 | 2975, 1738, 1598, 1489, 1277, 1235, 1041, 1026, 873, 759 |
| 91 | 2-Br | —$CH_2O$— | $CH_3$ | $CH_3$ | | | |
| 92 | 3-Br | —$CH_2O$— | $CH_3$ | $CH_3$ | | | |
| 93 | 4-Br | —$CH_2O$— | $CH_3$ | $CH_3$ | | | |

-continued (I)

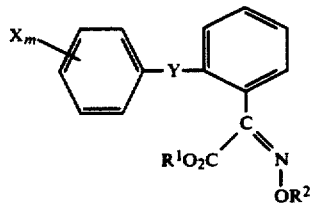

| Comp. No. | $X_m$ | Y | $R^1$ | $R^2$ | Isomer | Mp(°C.) | IR($cm^{-1}$) |
|---|---|---|---|---|---|---|---|
| 94 | 2,4-$Cl_2$ | —$CH_2O$— | $CH_3$ | $CH_3$ | | | |
| 95 | 2,6-$Cl_2$ | —$CH_2O$— | $CH_3$ | $CH_3$ | | | |
| 96 | 3,5-$Cl_2$ | —$CH_2O$— | $CH_3$ | $CH_3$ | | | |
| 97 | 2,4,6-$Cl_3$ | —$CH_2O$— | $CH_3$ | $CH_3$ | | | |
| 98 | 2-$CH_3$, 4-Cl | —$CH_2O$— | $CH_3$ | $CH_3$ | | | |
| 99 | 2-Cl, 4-$CH_3$ | —$CH_2O$— | $CH_3$ | $CH_3$ | | | |
| 100 | 2-$CH_3$ | —$CH_2O$— | $CH_3$ | $CH_3$ | E/Z | | 2970, 1735, 1489, 1454, 1278, 1231, 1045, 1025, 750 |
| 101 | 3-$CH_3$ | —$CH_2O$— | $CH_3$ | $CH_3$ | E/Z | 47–49 | 2970, 1736, 1600, 1490, 1453, 1279, 1227, 1045, 1026, 755 |
| 102 | 4-$CH_3$ | —$CH_2O$— | $CH_3$ | $CH_3$ | E/Z | 92–94 | 2970, 1736, 1600, 1490, 1454, 1278, 1232, 1043 1027, 761 |
| 103 | 4-$C_2H_5$ | —$CH_2O$— | $CH_3$ | $CH_3$ | | | |
| 104 | 4-i-$C_3H_7$ | —$CH_2O$— | $CH_3$ | $CH_3$ | | | |
| 105 | 4-t-$C_4H_9$ | —$CH_2O$— | $CH_3$ | $CH_3$ | | | |
| 106 | 2,4-$(CH_3)_2$ | —$CH_2O$— | $CH_3$ | $CH_3$ | | | |
| 107 | 2,6-$(CH_3)_2$ | —$CH_2O$— | $CH_3$ | $CH_3$ | | | |
| 108 | 2,4,6-$(CH_3)_3$ | —$CH_2O$— | $CH_3$ | $CH_3$ | | | |
| 109 | 2-$OCH_3$, 4-$CH_3$ | —$CH_2O$— | $CH_3$ | $CH_3$ | | | |
| 110 | 4-$OCH_3$, 2-$CH_3$ | —$CH_2O$— | $CH_3$ | $CH_3$ | | | |
| 111 | 2-$OCH_3$ | —$CH_2O$— | $CH_3$ | $CH_3$ | | | |
| 112 | 3-$OCH_3$ | —$CH_2O$— | $CH_3$ | $CH_3$ | | | |
| 113 | 4-$OCH_3$ | —$CH_2O$— | $CH_3$ | $CH_3$ | | | |
| 114 | 4-$OC_2H_5$ | —$CH_2O$— | $CH_3$ | $CH_3$ | | | |
| 115 | 4-O-i-$C_3H_7$ | —$CH_2O$— | $CH_3$ | $CH_3$ | | | |
| 116 | 2-$CF_3$ | —$CH_2O$— | $CH_3$ | $CH_3$ | | | |
| 117 | 3-$CF_3$ | —$CH_2O$— | $CH_3$ | $CH_3$ | | | |
| 118 | 4-$CF_3$ | —$CH_2O$— | $CH_3$ | $CH_3$ | | | |
| 119 | 2-CN | —$CH_2O$— | $CH_3$ | $CH_3$ | | | |
| 120 | 4-CN | —$CH_2O$— | $CH_3$ | $CH_3$ | | | |
| 121 | 3-$NO_2$ | —$CH_2O$— | $CH_3$ | $CH_3$ | | | |
| 122 | 4-$NO_2$ | —$CH_2O$— | $CH_3$ | $CH_3$ | | | |
| 123 | 4-$C_6H_5$ | —$CH_2O$— | $CH_3$ | $CH_3$ | | | |
| 124 | H | —$OCH_2$— | $CH_3$ | $CH_3$ | E/Z | oil | 2940, 1742 1598, 1496 1239, 1227 1046, 1019 755 |
| 125 | 2-F | —$OCH_2$— | $CH_3$ | $CH_3$ | | | |
| 126 | 2-Cl | —$OCH_2$— | $CH_3$ | $CH_3$ | | | |
| 127 | 4-Cl | —$OCH_2$— | $CH_3$ | $CH_3$ | | | |
| 128 | 2,4-$Cl_2$ | —$OCH_2$— | $CH_3$ | $CH_3$ | | | |
| 129 | 2-$CH_3$, 4-Cl | —$OCH_2$— | $CH_3$ | $CH_3$ | | | |
| 130 | 2-$CH_3$ | —$OCH_2$— | $CH_3$ | $CH_3$ | | | |
| 131 | 4-$CH_3$ | —$OCH_2$— | $CH_3$ | $CH_3$ | | | |
| 132 | 4-t-$C_4H_9$ | —$OCH_2$— | $CH_3$ | $CH_3$ | | | |
| 133 | 2-$OCH_3$ | —$OCH_2$— | $CH_3$ | $CH_3$ | | | |
| 134 | 2-$CF_3$ | —$OCH_2$— | $CH_3$ | $CH_3$ | | | |
| 135 | 4-$NO_2$ | —$OCH_2$— | $CH_3$ | $CH_3$ | | | |
| 136 | H | ethynylene | $CH_3$ | $CH_3$ | | | |
| 137 | 2-F | ethynylene | $CH_3$ | $CH_3$ | | | |
| 138 | 2-Cl | ethynylene | $CH_3$ | $CH_3$ | | | |
| 139 | 2-Br | ethynylene | $CH_3$ | $CH_3$ | | | |
| 140 | 4-Br | ethynylene | $CH_3$ | $CH_3$ | | | |
| 141 | 2-$CH_3$ | ethynylene | $CH_3$ | $CH_3$ | | | |
| 142 | 4-$CH_3$ | ethynylene | $CH_3$ | $CH_3$ | | | |
| 143 | 2-$OCH_3$ | ethynylene | $CH_3$ | $CH_3$ | | | |
| 144 | 4-$CF_3$ | ethynylene | $CH_3$ | $CH_3$ | | | |
| 145 | 2-$NO_2$ | ethynylene | $CH_3$ | $CH_3$ | | | |

-continued (I)

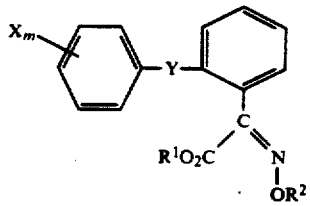

| Comp. No. | $X_m$ | Y | $R^1$ | $R^2$ | Isomer | Mp(°C.) | IR($cm^{-1}$) |
|---|---|---|---|---|---|---|---|
| 146 | H | —CH=CH— | $CH_3$ | H | | | |
| 147 | H | —$CH_2$—$CH_2$— | $CH_3$ | H | | | |
| 148 | H | —CH=CH— | $CH_3$ | $C_2H_5$ | | | |
| 149 | H | —$CH_2$—$CH_2$— | $CH_3$ | $C_3H_7$ | | | |
| 150 | H | —CH=CH— | $CH_3$ | $C_3H_7$ | | | |
| 151 | H | —$CH_2$—$CH_2$— | $CH_3$ | i-$C_3H_7$ | | | |
| 152 | H | —$CH_2$—$CH_2$— | $CH_3$ | t-$C_4H_9$ | | | |
| 153 | H | —$CH_2$—$CH_2$— | $CH_3$ | $C_5H_{11}$ | | | |
| 154 | H | —CH=CH— | $C_2H_5$ | $CH_3$ | | | |
| 155 | H | —$CH_2$—$CH_2$— | $C_2H_5$ | $CH_3$ | | | |
| 156 | H | —CH=CH— | i-$C_3H_7$ | $CH_3$ | | | |
| 157 | H | —$CH_2$—$CH_2$— | i-$C_3H_7$ | $CH_3$ | | | |
| 158 | H | —CH=CH— | $C_2H_5$ | $C_2H_5$ | | | |
| 159 | H | —$CH_2$—$CH_2$— | $C_2H_5$ | $C_2H_5$ | | | |
| 160 | H | O | $CH_3$ | $CH_3$ | | | |
| 161 | 2-F | O | $CH_3$ | $CH_3$ | | | |
| 162 | 2-Cl | O | $CH_3$ | $CH_3$ | | | |
| 163 | 2-Br | O | $CH_3$ | $CH_3$ | | | |
| 164 | 4-Br | O | $CH_3$ | $CH_3$ | | | |
| 165 | 4-Cl | O | $CH_3$ | $CH_3$ | | | |
| 166 | 2-$CH_3$ | O | $CH_3$ | $CH_3$ | | | |
| 167 | 4-$CH_3$ | O | $CH_3$ | $CH_3$ | | | |
| 168 | 2-$OCH_3$ | O | $CH_3$ | $CH_3$ | | | |
| 169 | 4-$OCH_3$ | O | $CH_3$ | $CH_3$ | | | |
| 170 | 4-$C_6H_5$ | O | $CH_3$ | $CH_3$ | | | |
| 171 | H | —CH=CH— | H | H | | | |
| 172 | H | —$CH_2$—$CH_2$— | H | H | | | |
| 173 | 4-$OCH_2$—$C_6H_5$ | —CH=$CH_2$— | $CH_3$ | $CH_3$ | | | |
| 174 | 4-$OCH_2$—$C_6H_5$ | —$CH_2$—$CH_2$— | $CH_3$ | $CH_3$ | | | |
| 175 | 4-$OC_6H_5$ | —CH=CH— | $CH_3$ | $CH_3$ | | | |
| 176 | 4-$OC_6H_5$ | —$CH_2$—$CH_2$— | $CH_3$ | $CH_3$ | | | |
| 177 | 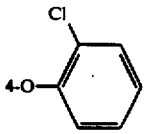 | —$CH_2$—$CH_2$— | $CH_3$ | $CH_3$ | | | |
| 178 | 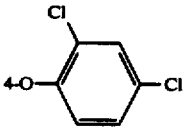 | —$CH_2$—$CH_2$— | $CH_3$ | $CH_3$ | | | |
| 179 | 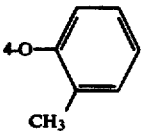 | —$CH_2$—$CH_2$— | $CH_3$ | $CH_3$ | | | |
| 180 | 3-$OCH_2$—$C_6H_5$ | —$CH_2$—$CH_2$— | $CH_3$ | $CH_3$ | | | |
| 181 | 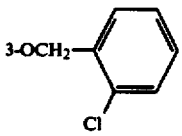 | —$CH_2$—$CH_2$— | $CH_3$ | $CH_3$ | | | |

-continued
(I)
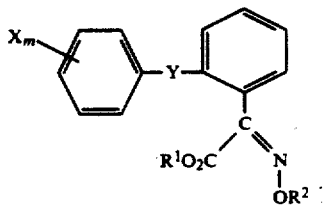
| Comp. No. | $X_m$ | Y | $R^1$ | $R^2$ | Isomer | Mp(°C.) | IR($cm^{-1}$) |
|---|---|---|---|---|---|---|---|
| 182 | 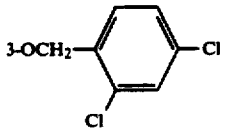 | $-CH_2-CH_2-$ | $CH_3$ | $CH_3$ | | | |
| 183 | 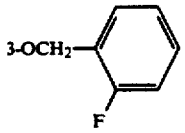 | $-CH_2-CH_2-$ | $CH_3$ | $CH_3$ | | | |
| 184 | 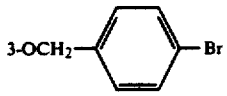 | $-CH_2-CH_2-$ | $CH_3$ | $CH_3$ | | | |
| 185 | 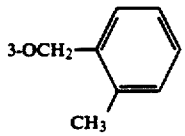 | $-CH_2-CH_2-$ | $CH_3$ | $CH_3$ | | | |
| 186 | $3\text{-}OC_6H_5$ | $-CH_2-CH_2-$ | $CH_3$ | $CH_3$ | | | |
| 187 | 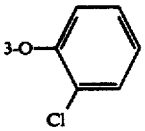 | $-CH_2-CH_2-$ | $CH_3$ | $CH_3$ | | | |
| 188 | 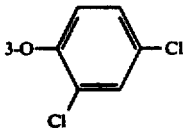 | $-CH_2-CH_2-$ | $CH_3$ | $CH_3$ | | | |
| 189 | 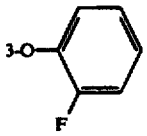 | $-CH_2-CH_2-$ | $CH_3$ | $CH_3$ | | | |
| 190 | 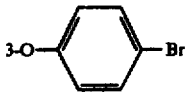 | $-CH_2-CH_2-$ | $CH_3$ | $CH_3$ | | | |

-continued (I)

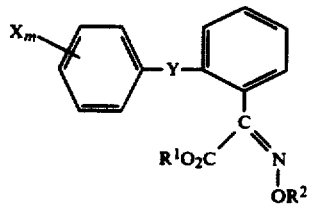

| Comp. No. | $X_m$ | Y | $R^1$ | $R^2$ | Isomer | Mp(°C.) | IR($cm^{-1}$) |
|---|---|---|---|---|---|---|---|
| 191 | 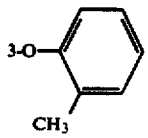 | $-CH_2-CH_2-$ | $CH_3$ | $CH_3$ | | | |

In general terms, the novel compounds are extremely effective on a broad spectrum of phytopathogenic fungi, in particular those from the class consisting of the Ascomycetes, Phycomycetes and Basidiomycetes. Some of them have a systemic action and can be used as foliar and soil fungicides.

The fungicidal compounds are of particular interest for controlling a large number of fungi in various crops or their seeds, especially wheat, rye, barley, oats, rice, Indian corn, cotton, soybeans, coffee, sugar cane, fruit and ornamentals in horticulture and viticulture, and in vegetables such as cucumbers, beans and cucurbits.

The novel compounds are particularly useful for controlling the following plant diseases:

Erysiphe graminis in cereals,
Erysiphe cichoracearum and Sphaerotheca fuliginea in cucurbits,
Podosphaera leucotricha in apples,
Uncinula necator in vines,
Puccinia species in cereals,
Rhizoctonia solani in cotton,
Ustilago species in cereals and sugar cane,
Venturia inaequalis (scab) in apples,
Septoria nodorum in wheat,
Pyrenophora teres in barley,
Botrytis cinerea (gray mold) in strawberries and grapes,
Cercaspora arachidicola in groundnuts,
Pseudocercosporella herpotrichoides in wheat and barley,
Pyricularia oryzae in rice,
Alternaria solani and Phytophthora infestans in potatoes and tomatoes,
Plasmopara viticola in grapes, and
Fusarium and Verticillum species in various plants.

The compounds are applied by spraying or dusting the plants with the active ingredients, or treating the seeds of the plants with the active ingredients. They may be applied before or after infection of the plants or seeds by the fungi.

The novel substances can be converted into conventional formulations such as solutions, emulsions, suspensions, dusts, powders, pastes and granules. The application forms depend entirely on the purposes for which they are intended; they should at all events ensure a fine and uniform distribution of the active ingredient. The formulations are produced in known manner, for example by extending the active ingredient with solvents and/or carriers, with or without the use of emulsifiers and dispersants; if water is used as solvent, it is also possible to employ other organic solvents as auxiliary solvents. Suitable auxiliaries for this purpose are solvents such as aromatics (e.g., xylene, benzene), chlorinated aromatics (e.g., chlorobenzenes), paraffins (e.g., crude oil fractions), alcohols (e.g., methanol, butanol), amines (e.g., ethanolamine, dimethylformamide), and water; carriers such as ground natural minerals (e.g., kaolins, aluminas, talc and chalk) and ground synthetic minerals (e.g., highly disperse silica and silicates); emulsifiers such as nonionic and anionic emulsifiers (e.g., polyoxyethylene fatty alcohol ethers, alkyl sulfonates and aryl sulfonates); and dispersants such as lignin, sulfite waste liquors and methylcellulose.

The fungicides generally contain from 0.1 to 95, and preferably from 0.5 to 90, wt % of active ingredient.

The application rates are from 0.5 to 3 kg or more of active ingredient per hectare, depending on the type of effect desired. The novel compounds may also be used for protecting materials, inter alia for combating wood-destroying fungi such as Coniophora puteana and Pllystictus versicolor. The novel active ingredients may also be used as fungicidal components of oily wood preservatives for protecting wood against wood-discoloring fungi. They are applied by treating, for example impregnating or painting, the wood with them.

The agents and the ready-to-use formulations prepared from them, such as solutions, emulsions, suspensions, powders, dusts, pastes and granules, are applied in conventional manner, for example by spraying, atomizing, dusting, scattering, dressing or watering.

Examples of formulations are given below.

I. 90 parts by weight of compound no. 83 is mixed with 10 parts by weight of N-methyl-alpha-pyrrolidone. A mixture is obtained which is suitable for application in the form of very fine drops.

II. 20 parts by weight of compound no. 124 is dissolved in a mixture consisting of 80 parts by weight of xylene, 10 parts by weight of the adduct of 8 to 10 moles of ethylene oxide and 1 mole of oleic acid-N-monoethanolamide, 5 parts by weight of the calcium salt of dodecylbenzene-sulfonic acid, and 5 parts by weight of the adducts of 40 moles of ethylene oxide and 1 mole of castor oil. By pouring the solution into water and uniformly distributing it therein, an aqueous dispersion is obtained.

III. 20 parts by weight of compound no. 83 is dissolved in a mixture consisting of 40 parts by weight of cyclohexanone, 30 parts by weight of isobutanol, 20 parts by weight of the adduct of 7 moles of ethylene oxide and 1 mole of isooctylphenol, and 10 parts by weight of the adduct of 40 moles of ethylene oxide and 1 mole of castor oil. By pouring the solution into water and finely distributing it therein, an aqueous dispersion is obtained.

IV. 20 parts by weight of compound no. 124 is dissolved in a mixture consisting of 25 parts by weight of cyclohexanol, 65 parts by weight of a mineral oil fraction having a boiling point between 210° and 280° C., and 10 parts by weight of the adduct of 40 moles of ethylene oxide and 1 mole of castor oil. By pouring the solution into water and uniformly distributing it therein, an aqueous dispersion is obtained.

V. 80 parts by weight of compound no. 83 is well mixed with 3 arts by weight of the sodium salt of diisobutylnaphthalene-alpha-sulfonic acid, 10 parts by weight of the sodium salt of a lignin-sulfonic acid obtained from a sulfite waste liquor, and 7 parts by weight of powdered silica gel, and triturated in a hammer mill. By uniformly distributing the mixture in water, a spray liquor is obtained.

VI. 3 parts by weight of compound no. 124 is intimately mixed with 97 parts by weight of particulate kaolin. A dust is obtained containing 3% by weight of the active ingredient.

VII. 30 parts by weight of compound no. 83 is intimately mixed with a mixture consisting of 92 parts by weight of powdered silica gel and 8 parts by weight of paraffin oil which has been sprayed onto the surface of this silica gel. A formulation of the active ingredient is obtained having good adherence.

VIII. 40 parts by weight of compound no. 124 is intimately mixed with 10 parts of the sodium salt of a phenolsulfonic acid-urea-formaldehyde condensate, 2 parts of silica gel and 48 parts of water to give a stable aqueous dispersion. Dilution in water gives an aqueous dispersion.

IX. 20 parts by weight of compound no. 83 is intimately mixed with 2 parts by weight of the calcium salt of dodecylbenzenesulfonic acid, 8 parts by weight of a fatty alcohol polyglycol ether, 2 parts by weight of the sodium salt of a phenolsulfonic acid-urea-formaldehyde condensate and 68 parts by weight of a paraffinic mineral oil. A stable oily dispersion is obtained.

In these application forms, the agents according to the invention may also be present together with other active ingredients, for example herbicides, insecticides, growth regulators, and fungicides, and may furthermore be mixed and applied together with fertilizers. Admixture with other fungicides frequently results in a greater fungicidal action spectrum.

The following list of fungicides with which the novel compounds may be combined is intended to illustrate possible combinations but not to impose any restrictions.

Examples of fungicides which may be combined with the novel compounds are:

sulfur,
dithiocarbamates and their derivatives, such as ferric dimethyldithiocarbamate,
zinc dimethyldithiocarbamate,
zinc ethylenebisdithiocarbamate,
manganese ethylenebisdithiocarbamate,
manganese zinc ethylenediaminebisdithiocarbamate,
tetramethylthiuram disulfides,
ammonia complex of zinc N,N'-ethylenebisdithiocarbamate,
ammonia complex of zinc N,N'-propylenebisdithiocarbamate,
zinc N,N'-propylenebisdithiocarbamate and
N,N'-polypropylenebis (thiocarbamyl) disulfide;
nitro derivatives, such as
dinitro(1-methylheptyl)-phenyl crotonate,
2-sec-butyl-4,6-dinitrophenyl 3,3-dimethylacrylate,
2-sec-butyl-4,6-dinitrophenyl isopropylcarbonate and
diisopropyl 5-nitroisophthalate;
heterocyclic substances, such as
2-heptadecylimidazole-2-yl acetate,
2,4-dichloro-6-(o-chloroanilino)-s-triazine,
O,O-diethyl phthalimidophosphonothioate,
5-amino-1-[-bis-(dimethylamino)-phosphinyl]-3-phenyl-1,2,4-triazole,
2,3-dicyano-1,4-dithiaanthraquinone,
2-thio-1,3-dithio[4,5-b]quinoxaline,
methyl 1-(butylcarbamyl)-2-benzimidazolecarbamate,
2-methoxycarbonylaminobenzimidazole,
2-(fur-2-yl)-benzimidazole,
2-(thiazol-4-yl)benzimidazole,
N-(1,1,2,2-tetrachloroethylthio)-tetrahydrophthalimide,
N-trichloromethylthiotetrahydrophthalimide,
N-trichloromethylthiophthalimide,
N-dichlorofluoromethylthio-N',N'-dimethyl-N-phenylsulfuric acid diamide,
5-ethoxy-3-trichloromethyl-1,2,3-thiadiazole,
2-thiocyanatomethylthiobenzothiazole,
1,4-dichloro-2,5-dimethoxybenzene,
4-(2-chlorophenylhydrazono)-3-methyl-5-isoxazolone,
2-thiopyridine 1-oxide,
8-hydroxyquinoline and its copper salt,
2,3-dihydro-5-carboxanilido-6-methyl-1,4-oxathiin,
2,3-dihydro-5-carboxanilido-6-methyl-1,4-oxathiin 4,4-dioxide,
2-methyl-5,6-dihydro-5H-pyran-3-carboxanilide,
2-methylfuran-3-carboxanilide,
2,5-dimethylfuran-3-carboxanilide,
2,4,5-trimethylfuran-3-carboxanilide,
2,5-dimethyl-N-cyclohexylfuran-3-carboxamide,
N-cyclohexyl-N-methoxy-2,5-diethylfuran-3-carboxamide,
2-methylbenzanilide,
2-iodobenzanilide,
N-formyl-N-morpholine-2,2,2-trichloroethylacetal, piperazine-1,4-diylbis-(1-(2,2,2-trichloroethyl)-formamide),
1-(3,4-dichloroanilino)-1-formylamino-2,2,2-trichloroethane, 2,6-dimethyl-N-tridecylmorpholine and its salts,
2,6-dimethyl-N-cyclododecylmorpholine and its salts,
N-[3-(p-tert.-butylphenyl)-2-methylpropyl]-cis-2,6-dimethylmorpholine,
N-[3-(p-tert.butylphenyl)-2-methylpropyl]-piperidine,
1-[2-(2,4-dichlorophenyl)-4-ethyl-1,3-dioxolan-2-ylethyl]-1H-1,2,4-triazole,
1-[2-(2,4-dichlorophenyl)-4-n-propyl-1,3-dioxolan-2-ylethyl]-1H-1,2,4-triazole,
N-(n-propyl)-N-(2,4,6-trichlorophenoxyethyl)-N'-imidazolyl-urea,
1-(4-chlorophenoxy)3,30367 -dimethyl-1-(1H-1,2,4-triazol-1-yl)-butan-2-one,
1-(4-chlorophenoxy)3,3-dimethyl-1-(1H-1,2,4-triazol-1-yl)butan-2-ol, α-(2-chlorophenyl)-α-(4-chlorophenyl)-5-pyrimidinemethanol,
5-butyl-(2-dimethylamino-4-hydroxy-6-methylpyrimidine,
bis-(p-chlorophenyl)-3-pyridinemethanol,
1,2-bis-(3-ethoxycarbonyl-2-thioureido)-benzene,
1,2-bis-(3-methoxycarbonyl-2-thioureido)-benzene, and various fungicides, such as
dodecylguanidine acetate,
3-[3-(3,5-dimethyl-2-oxycyclohexyl)-2-hydroxyethyl]-glutaramide,
hexachlorobenzene,
DL-methyl-N-(2,6-dimethylphenyl)-N-fur-2-yl alanate,
methyl DL-N-(2,6-dimetehylphenyl)-N-(2'-methoxyacetyl)-alanate,
N-(2,6-dimethylphenyl)-N-chloroacetyl-DL-2-aminobutyrolactone,
methyl DL-N-(2,6-dimethylphenyl)-N-(phenylacetyl-)alanate,
5-methyl-5-vinyl-3-(3,5-dichlorophenyl)-2,4-dioxo-1,3-oxazolidine,
3[3,5-dichlorophenyl]-5-methyl-5-methoxymethyl-1,3-oxazolidine-2,4-dione,
3-(3,5-dichlorophenyl)-1-isopropylcarbamylhydantoin,
N-(3,5-dichlorophenyl)-1,2-dimethylcyclopropane-1,2-dicarboximide,
2-cyano-[N-(ethylaminocarbonyl)-2-methoximino]acetamide,
1-[2-(2,4-dichlorophenyl)-pentyl]-1H-1,2,4-triazole,
2,4-difluoro-α-(1H-1,2,4-triazol-1-ylmethyl)-benzhydryl alcohol,
N-(3-chloro-2,6-dinitro-4-trifluoromethylphenyl)-5-trifluoromethyl-3-chloro-2-aminopyridine, and
1-((bis-(4-fluorophenyl)-methylsilyl)-methyl)-1H-1,2,4-triazole.

For the following experiments, the prior art active ingredients N-tridecyl-2,6-dimethylmorpholine (A), its acetate (B) and methyl 2-(4-[p-chlorostyryl]phenyl)-3-methoxyacrylate (C) were used for comparison purposes.

USE EXAMPLE 1

Action on wheat mildew

Leaves of pot-grown wheat seedlings of the "Frühgold" variety were sprayed with aqueous liquors containing (dry basis) 80% of active ingredient and 20% of emulsifier, and sprayed, 24 hours after the sprayed-on layer had dried, with spores of wheat mildew (Erysiphe graminis var. tritici). The plants were then set up in the greenhouse at 20° to 22° C. and a relative humidity of 75 to 80%. The extent of mildew spread was assessed after 7 days.

The results of this experiment show that active ingredients nos. 42, 49, 83, 100 and 124, applied as 0.025 and 0.006% (wt %) spray liquors, had a better fungicidal action (90%) than prior art active ingredients A, B and C (70%).

USE EXAMPLE 2

Action on Plasmopara viticola

Leaves of potted vines of the Müller-Thurgau variety were sprayed with aqueous suspensions containing (dry basis) 80% of active ingredient and 20% of emulsifier. To assess the duration of action, the plants were set up, after the sprayed-on layer had dried, for 8 days in the greenhouse. Then the leaves were infected with a zoospore suspension of Plasmopara viticola. The plants were first placed for 16 hours in a water vapor-saturated chamber at 24° C. and then in a greenhouse for 5 days at from 20° to 30° C. To accelerate and intensify the sporangiophore discharge, the plants were then again placed in the moist chamber for 16 hours. The extent of fungus attack was then assessed on the undersides of the leaves.

The results obtained in this experiment show that active ingredients nos. 42, 48, 83, 89, 100 and 124, applied as 0.05% spray liquors, had a good fungicidal action (90%).

USE EXAMPLE 3

Action on Septoria nodorum

Leaves of pot-grown wheat seedlings of the "Jubilar" variety were sprayed to runoff with aqueous liquors containing (dry basis) 80% of active ingredient and 20% of emulsifier. On the following day the plants were infected with an aqueous sport suspension of Septoria nodorum and further cultivated for 7 days at 17° to 19° C. and a relative humidity of 95%. The extent of fungus spread was then assessed visually.

The results obtained show that active ingredients nos. 49, 83 and 124, applied as 0.05% spray liquors, had a good fungicidal action (90%).

We claim:

1. An oxime ether of the formula I

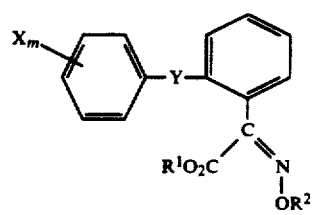

(I)

where $R^1$ is hydrogen or alkyl of 1 to 5 carbon atoms, $R^2$ is methyl, the radicals X (m=1 to 5) are identical or different substituents from the group consisting of halogen, cyano, trifluoromethyl, nitro, $C_1$–$C_4$-alkyl, $C_1$–$C_4$-alkoxy, phenyl, unsubstituted or halo or alkyl substituted phenoxy, unsubstituted or halo or alkyl substituted benzyloxy, and hydrogen, and Y is methyleneoxy, oxymethylene, ethylene, ethenylene, ethynylene or oxygen.

2. An oxime ether of the formula I as set forth in claim 1, where X is hydrogen, 2-fluoro, 3-fluoro, 4-fluoro, 2-chloro-6-fluoro, 2-chloro, 3-chloro, 4-chloro, 2-bromo, 3-bromo, 4-bromo, 2,4-dichloro, 2,6-dichloro, 3,5-dichloro, 2,4,6-trichloro, 2-chloro-4-methyl, 2-methyl-4-chloro, 2-methyl, 3-methyl, 4-methyl, 4-ethyl, 4-isopropyl, 4-tert.-butyl, 2,4-dimethyl, 2,6-dimethyl, 2,4,6-trimethyl, 2-methoxy-4-methyl, 4-methoxy-2-methyl, 2-methoxy, 3-methoxy, 4-methoxy, 4-ethoxy, 4-isopropoxy, 2-trifluoromethyl, 3-trifluoromethyl, 4-trifluoromethyl, 2-cyano, 4-cyano, 3-nitro, 4-nitro, 4-phenyl, 4-benzyloxy, 4-phenoxy, halophenoxy, 4-(2-chloro)-phenoxy, 4-(2,4-dichloro)-phenoxy, $C_1$–$C_4$-alkylphenoxy, 4-(2-methyl-phenoxy, 3-benzyloxy, halobenzyloxy, 3-(2-chloro)-benzyloxy, 3-(2,4-dichloro)-benzyloxy, 3-(2-fluoro)-benzyloxy, 3-(4-bromo)-benzyloxy-, $C_1$–$C_4$-alkylbenzyloxy, 3-(2-methyl)-benzyloxy, 3-phenoxy, 3-(2-chloro)-phenoxy, 3-(2,4-dichloro)-phenoxy, 3-(2-fluoro)-phenoxy, 3-(4-bromo)-phenoxy or 3-(2-methyl)-phenoxy, $R^1$ is hydrogen, methyl, ethyl or isopropyl.

3. A fungicidal agent containing an oxime ether of the formula I

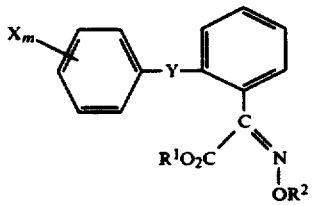

(I)

wherein $R^1$ is hydrogen or alkyl of 1 to 5 carbon atoms, $R^2$ is methyl, the radicals X (m=1 to 5) are identical or different substituents from the group consisting of halogen, cyano, trifluoromethyl, nitro, $C_1$–$C_4$-alkyl, $C_1$–$C_4$-alkoxy, phenyl, unsubstituted or halo or alkyl substituted phenoxy, unsubstituted or halo or alkyl substituted benzyloxy, and hydrogen, and Y is methyleneoxy, oxymethylene, ethylene, ethenylene, ethynylene or oxygen, and inert carriers.

4. A process for combating fungi, wherein an oxime ether of the formula I

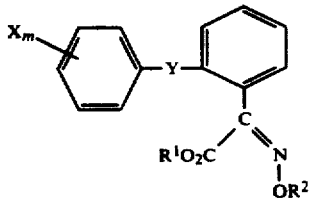

(I)

where $R^1$ and $R^2$ are identical or different and are each hydrogen or alkyl of 1 to 5 carbon atoms, the radicals X (m=1 to 5) are identical or different substituents from the group consisting of halogen, cyano, trifluoromethyl, nitro, $C_1$–$C_4$-alkyl, $C_1$–$C_4$-alkoxy, phenyl, unsubstituted or halo or alkyl substituted phenoxy, unsubstituted or halo or alkyl substituted benzyloxy, and hydrogen, and Y is methyleneoxy, oxymethylene, ethylene, ethenylene, ethynylene or oxygen, is allowed to act on the fungi, or the areas, plants, materials or seed threatened by fungus attack.

5. 2-Benzyloxyphenyl-glyoxylic acid methyl ester O-methyloxime.

6. 2-Phenyloxymethylenephenyl-glyoxylic acid methyl ester O-methyloxime.

7. The oxime ether according to claim 1, wherein Y is methyleneoxy.

8. The oxime ether according to claim 1, wherein Y is oxymethylene.

9. The oxime ether according to claim 1, wherein Y is ethylene.

10. The oxime ether according to claim 1, wherein Y is ethenylene.

11. The oxime ether according to claim 1, wherein Y is ethynylene.

12. The oxime ether according to claim 1, wherein Y is oxygen.

13. The oxime ether according to claim 2, wherein Y is —$CH_2O$—.

14. The oxime ether according to claim 2, wherein Y is —$OCH_2$—.

15. The oxime ether according to claim 2, wherein Y is —$CH_2CH_2$—.

16. The oxime ether according to claim 2, wherein Y is —CH=CH—.

17. The oxime ether according to claim 2, wherein Y is —C≡C—.

18. The oxime ether according to claim 2, wherein Y is —O—.

19. The fungicidal agent of claim 3, wherein in the oxime ether Y is methyleneoxy.

20. The fungicidal agent of claim 3, wherein in the oxime ether Y is oxymethylene.

21. The fungicidal agent of claim 3, wherein in the oxime ether Y is ethylene.

22. The fungicidal agent of claim 3, wherein in the oxime ether Y is ethenylene.

23. The fungicidal agent of claim 3, wherein in the oxime ether Y is ethynylene.

24. The fungicidal agent of claim 3, wherein in the oxime ether Y is oxygen.

25. The process according to claim 4, wherein in the oxime ether Y is methyleneoxy.

26. The process according to claim 4, wherein in the oxime ether Y is oxymethylene.

27. The process according to claim 4, wherein in the oxime ether Y is ethylene.

28. The process according to claim 4, wherein in the oxime ether Y is ethenylene.

29. The process according to claim 4, wherein in the oxime ether Y is ethynylene.

30. The process according to claim 4, wherein in the oxime ether Y is oxygen.

*31. The oxime ether of claim 1, wherein $R^1$ is methyl, Y is oxymethylene, m=1 or 2, when m=2, X is in the 2 and 4 positions and each X is selected from halogen or methyl, and wherein m=1, X is 2-halogen, 4-halogen, 2-methyl, 4-methyl or 2-methoxy.*

*32. The oxime ether of claim 31, wherein halogen is selected from the group consisting of fluorine and chlorine.*

* * * * *

UNITED STATES PATENT AND TRADEMARK OFFICE

CERTIFICATE OF CORRECTION

PATENT NO. : RE. 33,989

DATED : July 7, 1992

INVENTOR(S) : Bernd Wenderoth et al.

It is certified that error appears in the above-identified patent and that said Letters Patent is hereby corrected as shown below:

On the title page: Item [75]:

The third inventor's name is incorrect, should be, --Costin Rentzea--.

Signed and Sealed this

Twelfth Day of October, 1993

*Attest:*

Bruce Lehman

BRUCE LEHMAN

*Attesting Officer*

*Commissioner of Patents and Trademarks*